(12) United States Patent
Kobayashi et al.

(10) Patent No.: US 7,981,672 B2
(45) Date of Patent: Jul. 19, 2011

(54) MONOCLONAL ANTIBODY AND USE THEREOF

(75) Inventors: Hiroko Kobayashi, Fukushima (JP); Masahiro Hasegawa, Tsu (JP); Tsutomu Seito, Takasaki (JP)

(73) Assignee: Immuno-Biological Laboratories Co., Ltd., Fujioka-shi (JP)

( * ) Notice: Subject to any disclaimer, the term of this patent is extended or adjusted under 35 U.S.C. 154(b) by 91 days.

(21) Appl. No.: 12/440,645

(22) PCT Filed: Sep. 11, 2007

(86) PCT No.: PCT/JP2007/067666
§ 371 (c)(1),
(2), (4) Date: Mar. 10, 2009

(87) PCT Pub. No.: WO2008/032712
PCT Pub. Date: Mar. 20, 2008

(65) Prior Publication Data
US 2010/0111939 A1   May 6, 2010

(30) Foreign Application Priority Data

Sep. 11, 2006 (JP) ................. 2006-245966

(51) Int. Cl.
*A61K 39/395* (2006.01)
*C07K 16/28* (2006.01)
*C12N 5/20* (2006.01)
*G01N 33/53* (2006.01)

(52) U.S. Cl. ................. 435/326; 424/133.1; 424/139.1; 530/388.24; 530/388.25; 435/7.1

(58) Field of Classification Search .................. None
See application file for complete search history.

(56) References Cited

FOREIGN PATENT DOCUMENTS
WO        02 081522    10/2002

OTHER PUBLICATIONS

Mort et al. The use of cleavage site specific antibodies to delineate protein processing and breakdown pathways. J. Clin Patho:Mol Pathol 1999;52:11-18.*

Myles et al. Thrombin activatable fibrinolysis inhibitor, a potential regulator of vascular inflammation. J Biol Chem. Dec. 19, 2003;278(51):51059-67.*

Diao et al. Osteopontin as a mediator of NKT cell function in T cell-mediated liver diseases. Immunity. Oct. 2004;21(4):539-50.*

Harlow E, Lane D.. Antibodies a laboratory manual. Cold Spring Harbor, New York: Cold Spring Harbor Laboratory Press, pp. 141-155, 1989.*

Kon, S. et al., "Mapping of Functional Epitopes of Osteopontin by Monoclonal Antibodies Raised Against Degined Internal Sequences", Journal of Cellular Biochemistry, vol. 84, pp. 420-432, (2002).

Yokosaki, Y. et al., "The Integrin $\alpha_9 \beta$, binds to a novel recognition sequence (SVVYGLR) in the thrombin-cleaved amino-terminal fragment of osteopontin", The Journal of Biological Chemistry, vol. 274, No. 51, pp. 36328-36334, (1999).

Yamamoto, N. et al., "Essential role of the cryptic epitope SLAYGLR within osteopontin in a murine model of rheumatoid arthritis", The Journal of Clinical Investigation, vol. 112, No. 2, pp. 181-188, (2003).

Hotta, H. et al., "Detection of Various Epitopes of Murine Osteopontin by Monoclonal Antibodies", Biochemical and Biophysical Research Comminications, vol. 257, No. 1, pp. 6-11, (1999).

Erlanger, B.F. et al., Steroid-Protein Conjugates, The Journal of Biological Chemistry, vol. 234, No. 5, pp. 1090-1094, (1958).

Karu, A. E. et al., "Synthesis of Haptens and Derivation of Monoclonal Antibodies for Immunoassay of the Phenylurea Herbicide Diuron", J. Agric. Food Chem., vol. 42, Nol. 2, pp. 301-309, (1994).

Engvall, E. et al., "Enzyme Immunoassay ELISA and EMIT", Methods in Enzymology, vol. 70, pp. 419-431 (1980).

Kinebuchi, M. et al., "A Novel Cell Surface Antigen Involved in Thymocyte And Thymic Epithelial Cell Adhesion", The Journal of Immunology, vol. 146, Nol. 11, pp. 3721-3728, (1991).

* cited by examiner

*Primary Examiner* — Maher M Haddad
(74) *Attorney, Agent, or Firm* — Oblon, Spivak, McClelland, Maier & Neustadt, L.L.P.

(57) ABSTRACT

The purpose of the invention is to provide an antibody which recognizes OPN N-half but does not recognize the full-length OPN, and its use. A monoclonal antibody which is characterized in that it recognizes a protein or polypeptide in which the C-terminal amino acid sequence is YGLR (SEQ ID NO: 1) and it substantially does not recognize a protein or polypeptide which has an amino acid sequence of YGLR outside of the C-terminal, as well as a method for measuring OPN N-half utilizing the said antibody, a method for diagnosing diseases relating to OPN N-half, a method for judging the severity of said disease, and a method for treating said diseases, are provided.

13 Claims, 6 Drawing Sheets

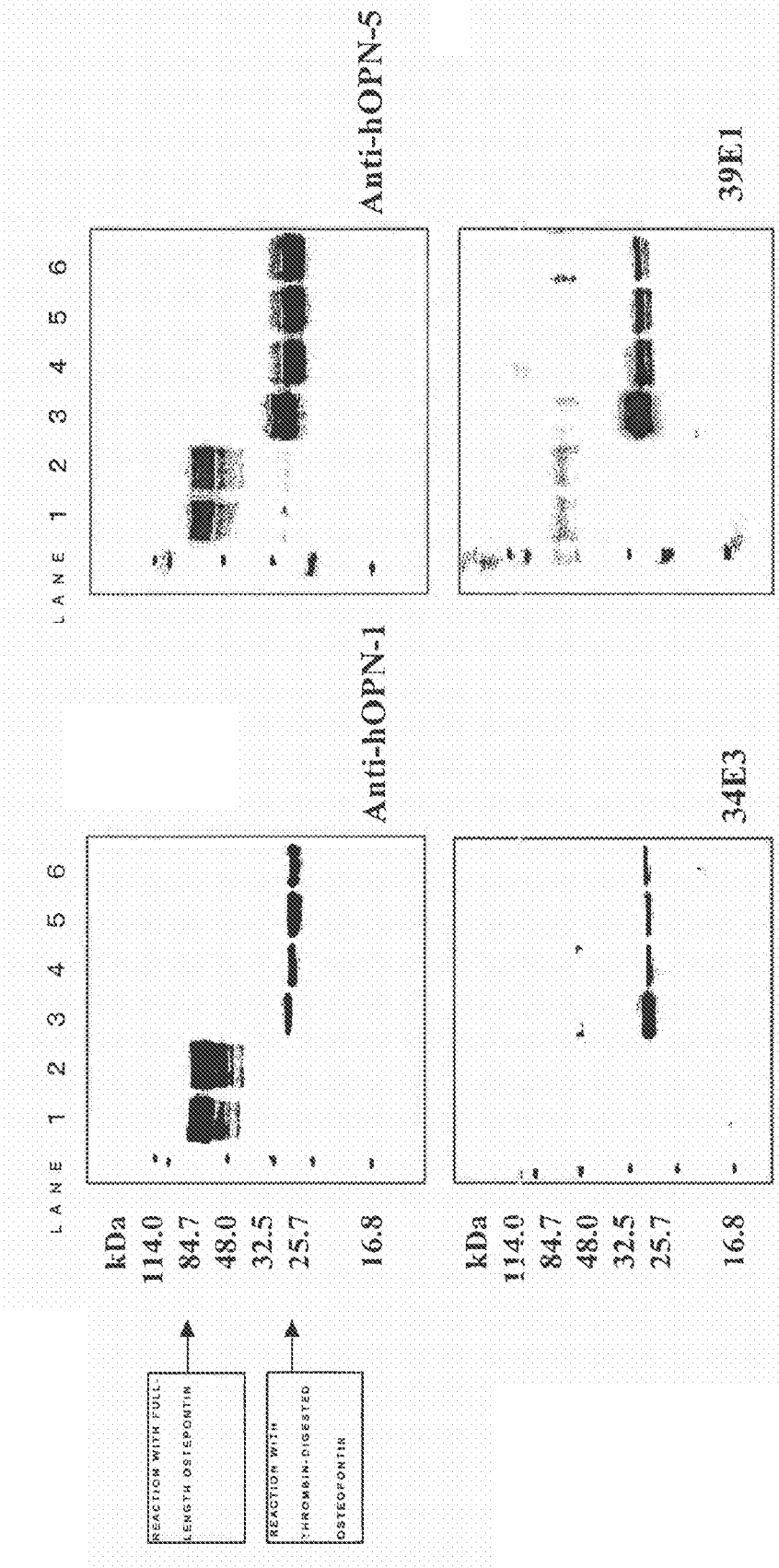

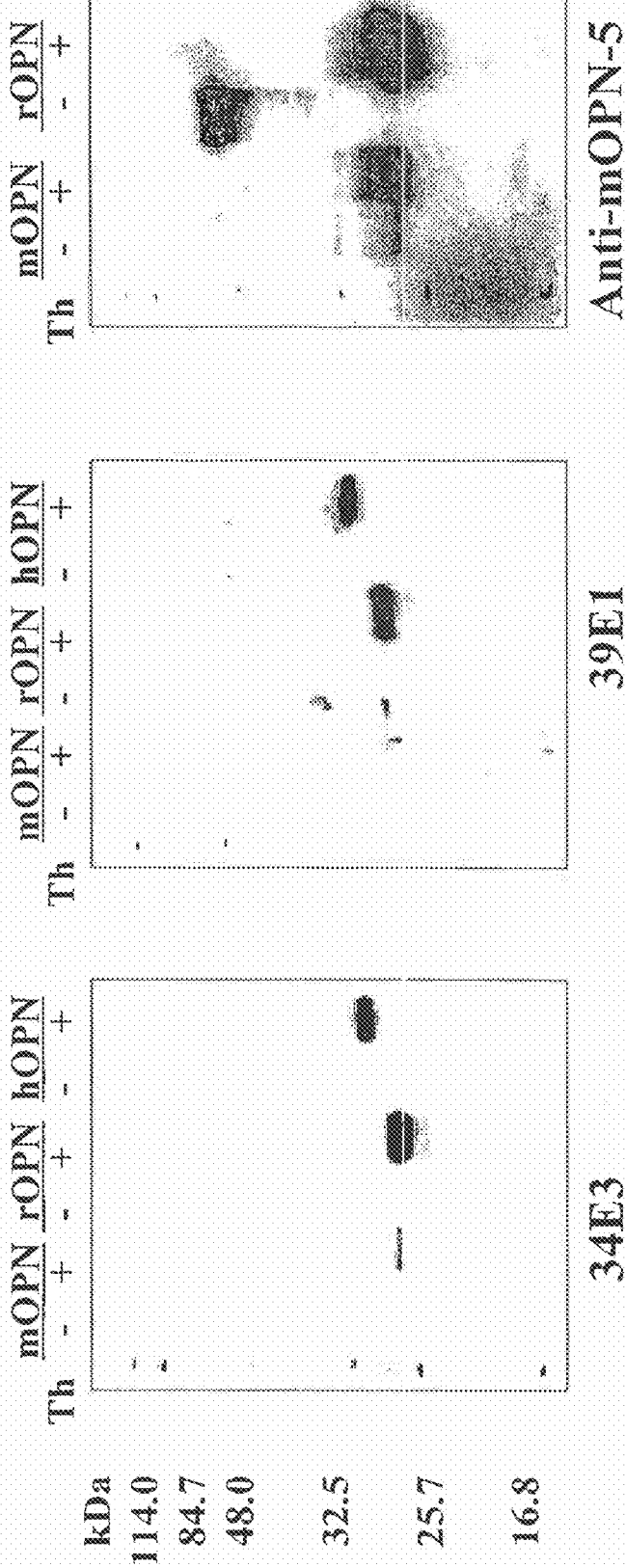
[FIG. 2]

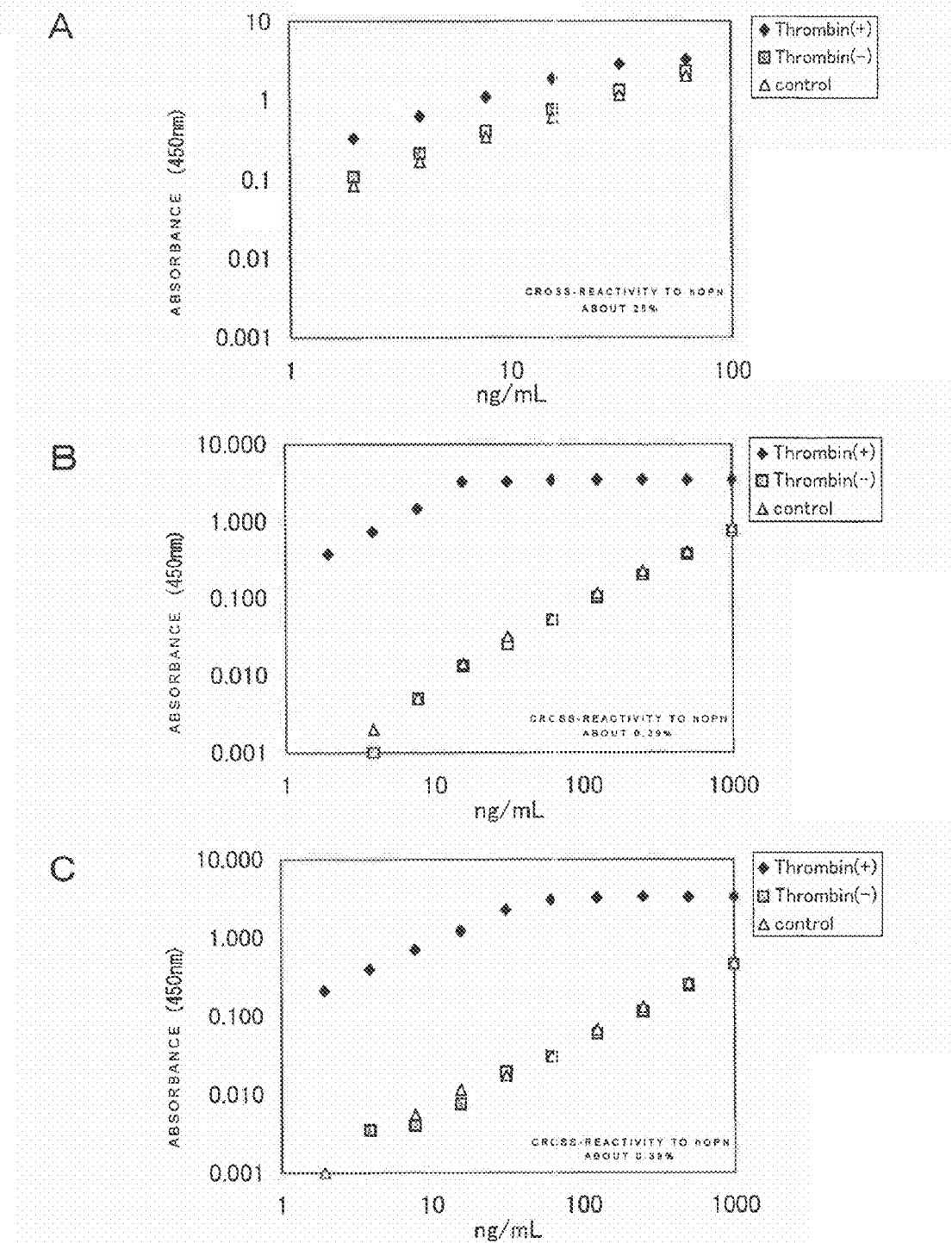

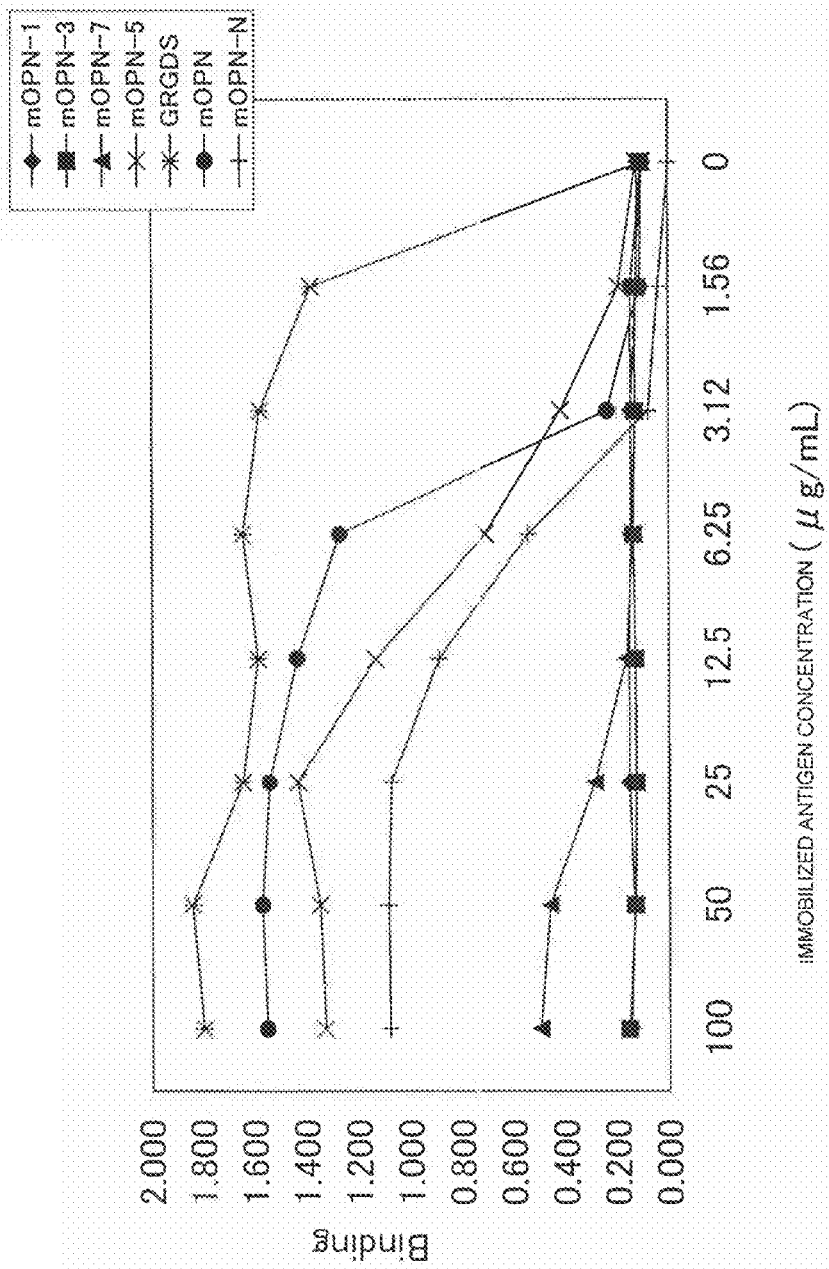
[FIG. 4]

[FIG. 5]
A
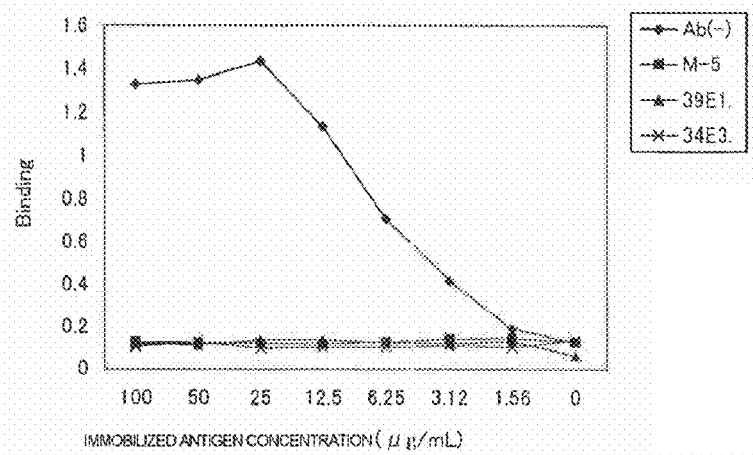
B
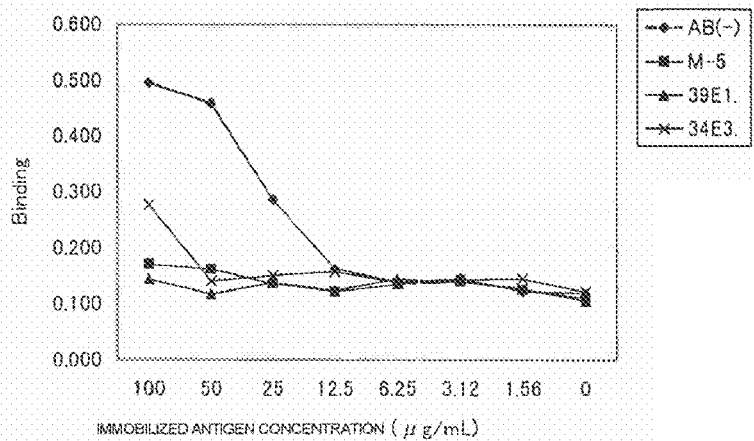
C
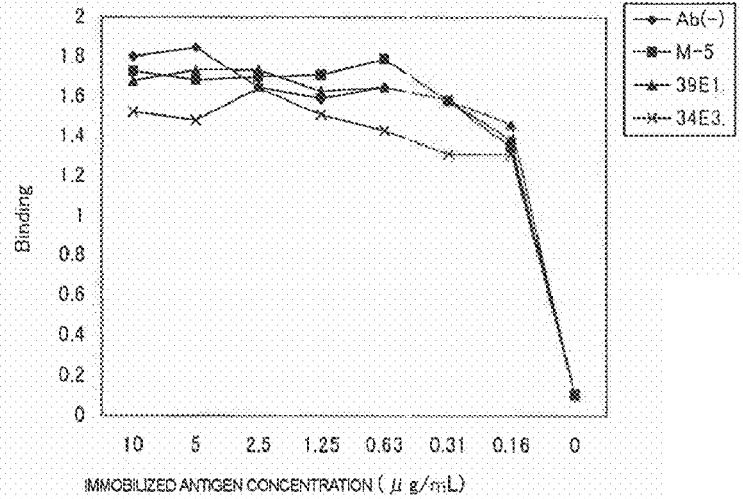

[FIG. 6]
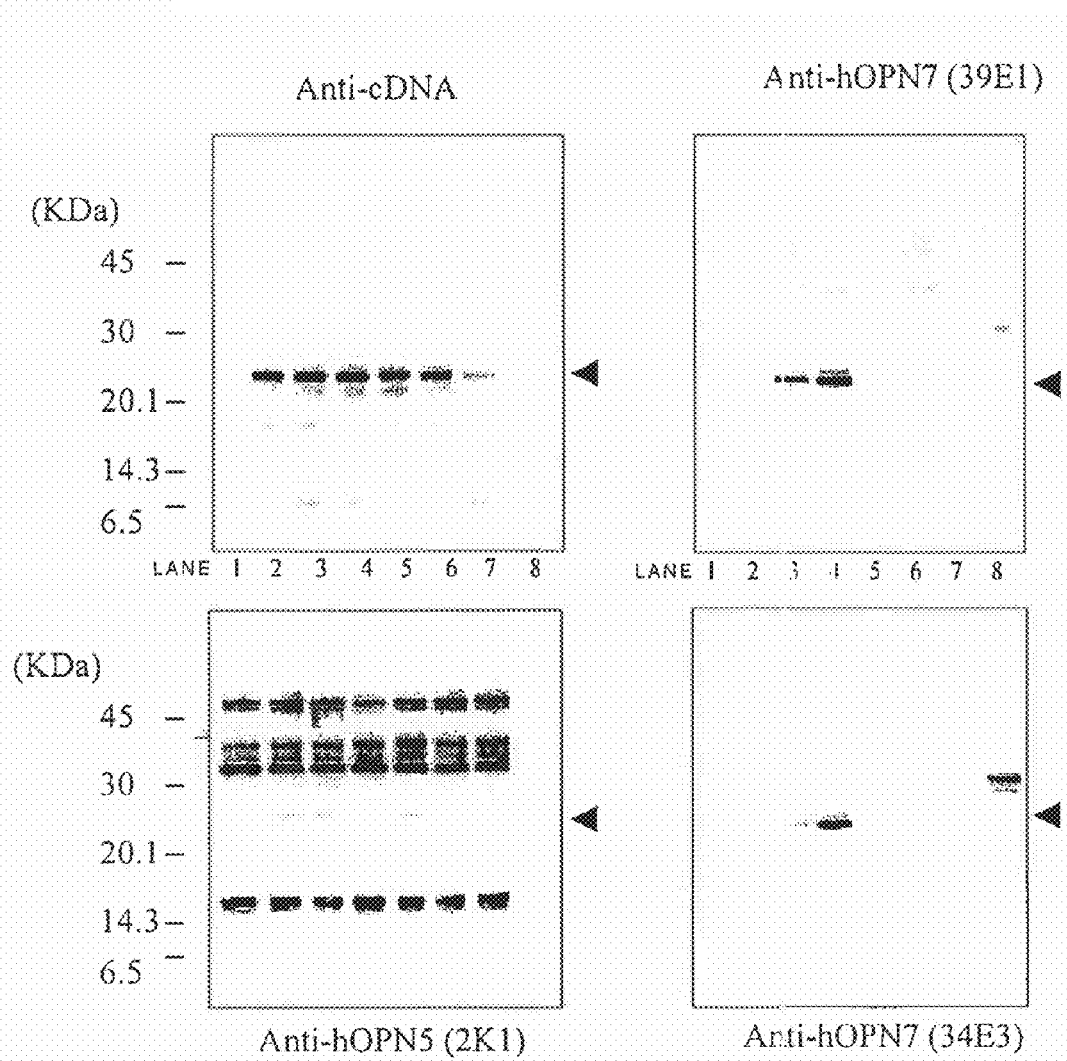

SEQUENCE LISTING

<160> NUMBER OF SEQ ID NOS: 20

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Tyr Gly Leu Arg
1

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

Ser Val Val Tyr Gly Leu Arg
1               5

<210> SEQ ID NO 3
<211> LENGTH: 314
<212> TYPE: PRT
<213> ORGANISM: Homo sapiens

<400> SEQUENCE: 3

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Glu Asp Asp Asp His
                85                  90                  95

Val Asp Ser Gln Asp Ser Ile Asp Ser Asn Asp Ser Asp Asp Val Asp
                100                 105                 110

Asp Thr Asp Asp Ser His Gln Ser Asp Glu Ser His His Ser Asp Glu
            115                 120                 125

Ser Asp Glu Leu Val Thr Asp Phe Pro Thr Asp Leu Pro Ala Thr Glu
130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser

```
                210                 215                 220
Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
                260                 265                 270

Phe His Ser His Glu Phe His Ser His Glu Asp Met Leu Val Val Asp
                275                 280                 285

Pro Lys Ser Lys Glu Glu Asp Lys His Leu Lys Phe Arg Ile Ser His
                290                 295                 300

Glu Leu Asp Ser Ala Ser Ser Glu Val Asn
305                 310

<210> SEQ ID NO 4
<211> LENGTH: 294
<212> TYPE: PRT
<213> ORGANISM: Mus musculus

<400> SEQUENCE: 4

Met Arg Leu Ala Val Ile Cys Phe Cys Leu Phe Gly Ile Ala Ser Ser
1               5                   10                  15

Leu Pro Val Lys Val Thr Asp Ser Gly Ser Ser Glu Glu Lys Leu Tyr
                20                  25                  30

Ser Leu His Pro Asp Pro Ile Ala Thr Trp Leu Val Pro Asp Pro Ser
                35                  40                  45

Gln Lys Gln Asn Leu Leu Ala Pro Gln Asn Ala Val Ser Ser Glu Glu
                50                  55                  60

Lys Asp Asp Phe Lys Gln Glu Thr Leu Pro Ser Asn Ser Asn Glu Ser
65                  70                  75                  80

His Asp His Met Asp Asp Asp Asp Asp Asp Asp Asp Asp Asp Gly Asp
                    85                  90                  95

His Ala Gly Ser Glu Asp Ser Val Asp Ser Asp Glu Ser Asp Glu Ser
                100                 105                 110

His His Ser Asp Glu Ser Asp Glu Thr Val Thr Ala Ser Thr Gln Ala
                115                 120                 125

Asp Thr Phe Thr Pro Ile Val Pro Thr Val Asp Val Pro Asn Gly Arg
                130                 135                 140

Gly Asp Ser Leu Ala Tyr Gly Leu Arg Ser Lys Ser Arg Ser Phe Gln
145                 150                 155                 160

Val Ser Asp Glu Gln Tyr Pro Asp Ala Thr Asp Glu Asp Leu Thr Ser
                165                 170                 175

His Met Lys Ser Gly Glu Ser Lys Glu Ser Leu Asp Val Ile Pro Val
                180                 185                 190

Ala Gln Leu Leu Ser Met Pro Ser Asp Gln Asp Asn Asn Gly Lys Gly
                195                 200                 205

Ser His Glu Ser Ser Gln Leu Asp Glu Pro Ser Leu Glu Thr His Arg
                210                 215                 220

Leu Glu His Ser Lys Glu Ser Gln Glu Ser Ala Asp Gln Ser Asp Val
225                 230                 235                 240

Ile Asp Ser Gln Ala Ser Ser Lys Ala Ser Leu Glu His Gln Ser His
                245                 250                 255

Lys Phe His Ser His Lys Asp Lys Leu Val Leu Asp Pro Lys Ser Lys
                260                 265                 270

Glu Asp Asp Arg Tyr Leu Lys Phe Arg Ile Ser His Glu Leu Glu Ser
```

```
                    275                 280                 285

Ser Ser Ser Glu Val Asn
            290

<210> SEQ ID NO 5
<211> LENGTH: 317
<212> TYPE: PRT
<213> ORGANISM: Rattus norvegicus

<400> SEQUENCE: 5

Met Arg Leu Ala Val Cys Phe Cys Leu Phe Gly Leu Ala Ser Cys
1               5                   10                  15

Leu Pro Val Lys Val Ala Glu Phe Gly Ser Ser Glu Glu Lys Ala His
            20                  25                  30

Tyr Ser Lys His Ser Asp Ala Val Ala Thr Trp Leu Lys Pro Asp Pro
        35                  40                  45

Ser Gln Lys Gln Asn Leu Leu Ala Pro Gln Asn Ser Val Ser Ser Glu
    50                  55                  60

Glu Thr Asp Asp Phe Lys Gln Glu Thr Leu Pro Ser Asn Ser Asn Glu
65                  70                  75                  80

Ser His Asp His Met Asp Asp Asp Asp Asp Asp Asp Asp Gly Asp
                85                  90                  95

His Ala Glu Ser Glu Asp Ser Val Asn Ser Asp Glu Ser Asp Glu Ser
                100                 105                 110

His His Ser Asp Glu Ser Asp Glu Ser Phe Thr Ala Ser Thr Gln Ala
            115                 120                 125

Asp Val Leu Thr Pro Ile Ala Pro Thr Val Asp Val Pro Asp Gly Arg
    130                 135                 140

Gly Asp Ser Leu Ala Tyr Gly Leu Arg Ser Lys Ser Arg Ser Phe Pro
145                 150                 155                 160

Val Ser Asp Glu Gln Tyr Pro Asp Ala Thr Asp Glu Asp Leu Thr Ser
                165                 170                 175

Arg Met Lys Ser Gln Glu Ser Asp Glu Ala Leu Lys Val Ile Pro Val
                180                 185                 190

Ala Gln Arg Leu Ser Val Pro Ser Asp Gln Asp Ser Asn Gly Lys Thr
            195                 200                 205

Ser His Glu Ser Ser Gln Leu Asp Glu Pro Ser Val Glu Thr His Ser
    210                 215                 220

Leu Glu Gln Ser Lys Glu Tyr Lys Gln Arg Ala Ser His Glu Ser Thr
225                 230                 235                 240

Glu Gln Ser Asp Ala Ile Asp Ser Ala Glu Lys Pro Asp Ala Ile Asp
                245                 250                 255

Ser Ala Glu Arg Ser Asp Ala Ile Asp Ser Gln Ala Ser Ser Lys Ala
            260                 265                 270

Ser Leu Glu His Gln Ser His Glu Phe His Ser His Glu Asp Lys Leu
    275                 280                 285

Val Leu Asp Pro Lys Ser Lys Glu Asp Asp Arg Tyr Leu Lys Phe Arg
    290                 295                 300

Ile Ser His Glu Leu Glu Ser Ser Ser Ser Glu Val Asn
305                 310                 315

<210> SEQ ID NO 6
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Pro Val Lys Gln Ala Asp Ser Gly Ser Ser Glu Glu Lys Gln
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Pro Val Lys Val Thr Asp Ser Gly Ser Ser Glu Glu Lys Leu Tyr
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Pro Val Lys Val Ala Glu Phe Gly Ser Ser Glu Glu Lys Ala His
1               5                   10                  15

Tyr

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Ser Val Val Tyr Gly Leu Arg
1               5

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Pro Val Lys Gln Ala Asp Ser Gly Ser Ser Glu Glu Lys Gln Cys
1               5                   10                  15

<210> SEQ ID NO 11
<211> LENGTH: 18
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Val Asp Thr Tyr Asp Gly Arg Gly Asp Ser Val Val Tyr Gly Leu
1               5                   10                  15

Arg Ser

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Val Asp Val Pro Asn Gly Arg Gly Asp Ser Leu Ala Tyr Gly Leu
1               5                   10                  15

Arg

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ser Arg Ser Phe Gln Val Ser Asp Glu Gln Tyr Pro Asp Ala Thr
1               5                   10                  15

Asp Glu

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Asp Val Pro Asn Gly Arg Gly Asp Ser Leu Ala Tyr Gly Leu Arg
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Leu Ala Tyr Gly Leu Arg
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
```

-continued

```
peptide

<400> SEQUENCE: 16

Gly Arg Gly Asp Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Tyr Gly Leu Arg
1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Tyr Gly Leu
1

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Val Val Tyr Gly Leu
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Val Val Tyr Gly
1               5
```

MONOCLONAL ANTIBODY AND USE THEREOF

CROSS-REFERENCE TO RELATED APPLICATIONS

The present application is a 35 U.S.C. §371 National Stage patent application of International patent application PCT/JP2007/067666, filed on Sep. 11, 2007, which claims priority to Japanese patent application JP 2006-245966, filed on Sep. 11, 2006.

TECHNICAL FIELD

The present invention relates to a monoclonal antibody which specifically recognizes a protein or polypeptide containing a particular amino acid sequence at the C terminal, and to use thereof.

BACKGROUND ART

Osteopontin (hereinafter referred to as "OPN") is an acidic and calcium-binding glycoprotein abundant in bone. The matured OPN is cleaved in vivo by thrombin to yield two fragments, i.e., the N-terminal fragment of OPN (hereinafter referred to as "OPN N-half") and the C-terminal fragment (hereinafter referred to as "OPN C-half"). For example, human osteopontin (hereinafter referred to as "hOPN") is cleaved at the C-terminal 168th arginine on the hOPN amino acid sequence to yield two fragments, hOPN N-half and hOPN C-half.

The above-mentioned OPN has a variety of physiologically and pathologically important functions, for example, cell adhesion, cell migration, tumorigenesis, immune response and inhibition of complement-mediated cytolysis, etc. These various functions are mediated by a variety of cell-surface receptors. It has been elucidated that the OPN N-half cleaved by thrombin exposes the SVVYGLR (SEQ ID NO: 2) sequence at the C-terminal, through which OPN binds itself to integrin α9 or α4.

The applicant of the present invention has so far investigated the in vivo function of OPN and gradually made clear the relation between the above OPN N-half and a variety of diseases. For example, in the International Patent Application (Patent Document 1) filed by the applicant, it has been reported that the ratio of OPN N-half to the total OPN is increased in patients suffering from rheumatism.

Though the relation between OPN N-half and diseases has gradually been elucidated, it was very important to measure accurately OPN N-half in order to further make its relation with other diseases clear. The 2K1 antibody reported by the applicant in the above-identified International Patent Application, however, also recognizes the OPN not cleaved by thrombin in addition to the C-terminal recognition site of OPN N-half; thus, it was hard to say that OPN N-half can be accurately measured depending on conditions.

From the fact that the above OPN N-half cleaved from OPN by thrombin exposes the SVVYGLR (SEQ ID NO: 2) sequence, through which OPN binds itself to integrin α9 or α4, it was necessary to provide an antibody which specifically binds to at least one part of the above-mentioned sequence in order to inhibit the binding effectively.

Patent Document: WO02/081522 internationally published pamphlet

DISCLOSURE OF INVENTION

Problem to be Solved by the Invention

Thus, the purpose of the invention is to provide an antibody which recognizes OPN N-half but not the full length of OPN and a method for measuring precisely OPN N-half utilizing said antibody.

Means for Solving the Problems

The inventors of the present application worked assiduously to solve the above-mentioned problems, and found that the above problems could be solved by a monoclonal antibody which was obtained from a polypeptide comprising a particular amino acid sequence as an antigen and which specifically recognized a protein or polypeptide having a particular amino acid sequence at the C-terminal. Thus, the present invention was completed.

The inventors further found that OPN N-half could be measured precisely utilizing this monoclonal antibody. They further found that the above antibody could be utilized in diagnosis or treatment of a disease relating to OPN N-half or judgment of its severity. Even further, the inventors found that, since the above antibody recognizes a protein or peptide in which the C-terminal amino acid sequence was identical with the above-mentioned amino acid sequence, it could be utilized in detection and purification of an objective protein by means of using said protein or polypeptide as a tag. Thus, the invention was completed.

Specifically, the present invention provides a monoclonal antibody which recognize a protein or polypeptide in which the C-terminal amino acid sequence is YGLR (SEQ ID NO: 1) but substantially does not recognize a protein or polypeptide which has the amino acid sequence YGLR (SEQ ID NO: 1) outside of the C-terminal.

Further, the second invention provides a kit for measuring the N-terminal fragment of osteopontin cleaved by thrombin, which comprises a first reagent containing the above monoclonal antibody and a second reagent containing an antibody of which the recognition site is different from that of the antibody contained in the first reagent and which recognizes the N-terminal fragment of osteopontin cleaved by thrombin.

The present invention further provides a method for measuring the N-terminal fragment of osteopontin cleaved by thrombin, which comprises measuring the N-terminal fragment of osteopontin cleaved by thrombin in a sample with the above monoclonal antibody.

The present invention provides a method for diagnosing rheumatoid arthritis, a method for distinguishing rheumatoid arthritis and osteoarthritis, and/or a method for judging the severity of osteoarthritis, which comprises measuring the amount of the N-terminal fragment of osteopontin cleaved by thrombin in a sample with the above monoclonal antibody and using the measured amount as an index.

The present invention provides a therapeutic agent for inflammatory diseases comprising as an active ingredient the above monoclonal antibody, and a method for treating inflammatory diseases which comprises administering the therapeutic agent for inflammatory diseases to a patient suffering from inflammatory disease.

The present invention provides a therapeutic agent for autoimmune diseases comprising as an active ingredient the above monoclonal antibody, and a method for treating autoimmune diseases which comprises administering the therapeutic agent for autoimmune diseases to a patient suffering from autoimmune disease.

The present invention provides a method for detecting or purifying a target protein expressed together with a tag using a tag-recognizing antibody, which comprises using as a tag a protein or polypeptide in which the C-terminal amino acid sequence is YGLR (SEQ ID NO: 1) and further using the above monoclonal antibody as a tag-recognizing antibody.

Furthermore, the present invention provides a recombinant vector comprising a polynucleotide coding for a target protein and another polynucleotide coding for a protein or polypeptide in which the C-terminal amino acid sequence is YGLR (SEQ ID NO: 1).

Effect of the Invention

The monoclonal antibody of the invention, since it specifically recognizes a protein or polypeptide which has a particular amino acid sequence at the C-terminal, specifically recognizes OPN N-half in which the C-terminal amino acid sequence is identical with the above one but substantially does not recognize OPN which has said amino acid sequence outside of the C-terminal.

This monoclonal antibody, accordingly, can be utilized in precise measurement of OPN N-half recognized by said monoclonal antibody, diagnosis or treatment of a disease relating to OPN N-half or judgment of its severity, or detection, purification, etc of an objective protein containing as a tag said amino acid sequence specifically binding to the above antibody.

BEST MODE FOR CARRYING OUT THE INVENTION

The monoclonal antibody of the invention (hereinafter referred to as "antibody of the invention") is characterized in that it recognizes a protein or polypeptide in which the C-terminal amino acid sequence is YGLR (SEQ ID NO: 1), but it substantially does not recognize a protein or polypeptide which has the amino acid sequence YGLR (SEQ ID NO: 1) outside of the C-terminal. In this context, the phrase "substantially does not recognize a protein or polypeptide which has the amino acid sequence YGLR (SEQ ID NO: 1) outside of the C-terminal" means that the percentage of the above antibody binding to said protein or polypeptide is 1.0% by mass (hereinafter merely referred to as "%") or less, preferably 0-0.5%.

There is no particular limitation in a method for preparing the antibody of the invention, as far as the antibody has the above-mentioned characteristics. In preparing the antibody of the invention, specifically, an animal is immunized with a protein or polypeptide as an antigen containing an amino acid sequence of YGLR (SEQ ID NO: 1) at the C-terminal, followed by recovering the antibody from the animal through screening with a protein or polypeptide containing the amino acid sequence of YGLR (SEQ ID NO: 1) at the C-terminal and a protein or polypeptide containing the amino acid sequence of YGLR (SEQ ID NO: 1) outside of the C-terminal. The followings will illustrate a method for preparing the antibody of the invention in detail.

In the above protein or polypeptide used as an antigen in which the C-terminal amino acid sequence is YGLR (SEQ ID NO: 1), there is no particular limitation; for example, such a polypeptide includes those in which the C-terminal amino acid sequence is YGLR (SEQ ID NO: 1) and which contains sequentially about 4 to 10 amino acids, preferably about 5 to 7 amino acids, from the C-terminal to the N-terminal side of OPN N-half. A specific example of polypeptides is a polypeptide comprised of 7 consecutive amino acid sequence SVVYGLR (SEQ ID NO: 2) from the C-terminal to the N-terminal side of OPN N-half (hereinafter referred to as "hOPN-7 peptide"). The hOPN-7 peptide is identical with the 162nd to 168th amino acid sequence (SEQ ID NO: 3) of hOPN. In this connection, the amino acid sequence of hOPN can be seen as Accession Numbers BAA03554, AAC28619, etc. in Pubmed (http://www.ncbi.nim.nih.gov/entrez/query.fcgi?DB=pubmed); in this invention, the amino acid sequence from BAA03554 was employed as that of hOPN. In order to enhance antigenicity, it is preferable to link the above polypeptide to a biopolymer compound to form a conjugate, which is used as an antigen. In such a case, it is preferable to make cysteine (C) attach to the N-terminal amino acid of the above polypeptide.

The protein or polypeptide used as an antigen in which the C-terminal amino acid sequence is YGLR (SEQ ID NO: 1) may be prepared in various methods without any particular limitation. Among them, the polypeptide may be prepared, for example, in a method known in the field of the art, or purchased as a synthetic product from Synpep Corporation or TANA Laboratories, USA.

As examples of the biological high molecular compound bound with the peptide, keyhole limpet hemocyanin (KLH), ovalbumin (OVA), bovine serum albumin (BSA), rabbit serum albumin (RSA), thyroglobulin, and the like can be given. Among these, KLH and thyroglobulin are preferable.

The above-mentioned polypeptide can be bound with the biological high molecular compound by known methods such as a mixed acid anhydride method (B. F. Erlanger, et al., J. Biol. Chem., 234, 1090-1094 (1954)), an activated ester method (A. E. KARU, et al., J. Agric. Food Chem., 42, 301-309 (1994)), and the like.

_A mixed acid anhydride used in the mixed acid anhydride method is obtained by subjecting the above-mentioned polypeptide to a common Schotten-Baumann reaction. The resulting reaction product is reacted with the biological high molecular compound to obtain the target bound substance of the peptide and biological high molecular compound. As examples of the haloformate used in this mixed acid anhydride method, methyl chloroformate, methyl bromoformate, ethyl chloroformate, ethyl bromoformate, and isobutyl chloroformate can be given. The ratio of the peptide, haloformate, and high molecular compound used in this method can be appropriately selected from a wide range.

The Schotten-Baumann reaction is carried out in the presence of a basic compound. As the basic compound used for the reaction, compounds commonly used in the Schotten-Baumann reaction, for example, organic bases such as triethylamine, trimethylamine, pyridine, dimethylaniline, N-methylmorpholine, diazabicyclononene (DBN), diazabicycloundecene (DBU), and diazabicyclootane (DABCO), inorganic bases such as potassium carbonate, sodium carbonate, potassium hydrogen carbonate, and sodium hydrogencarbonate; and the like can be used.

The reaction is carried out at a temperature usually from −20° C. to 100° C., and preferably from 0° C. to 50° C., for 5 minutes to 10 hours, and preferably 5 minutes to 2 hours.

The reaction of the resulting mixed acid anhydride and the biological high molecular compound is carried out at a temperature usually from −20° C. to 150° C., and preferably from 0° C. to 100° C., for 5 minutes to 10 hours, and preferably 5 minutes to 5 hours. The mixed acid anhydride method is usually carried out in a solvent. Any solvents commonly used in the mixed acid anhydride method, for example, halogenated hydrocarbons such as dichloromethane, chloroform, and dichloroethane; aromatic hydrocarbons such as benzene, toluene, and xylene; ethers such as diethyl ether, dioxane, tetrahydrofuran, and dimethoxyethane; esters such as methyl acetate and ethyl acetate; aprotic polar solvents such as N,N-dimethylformamide, dimethyl sulfoxide, and triamide hexamethylphosphate, and the like can be given.

On the other hand, the activated ester method can be carried out as follows. First, the polypeptide is dissolved in an organic solvent and reacted with imide N-hydroxysuccinate in the presence of a coupling agent to produce activated imide N-hydroxysuccinate.

As the coupling agent used in this reaction, any coupling agents commonly used in a condensation reaction, for example, dicyclohexylcarbodiimide, carbonyldiimidazole, water-soluble carbodiimide, and the like can be used. As an organic solvent, for example, N,N-dimethylformamide (DMF), dimethyl sulfoxide, dioxane, and the like can be used. The molar ratio of the polypeptide and the coupling agent such as imide N-hydroxysuccinate used for the reaction is preferably from 1:10 to 10:1, and most preferably 1:1. The reaction is carried out at a temperature usually from 0° C. to 50° C., and preferably from 22° C. to 27° C., for 5 minutes to 24 hours, and preferably 1 to 2 hours. A reaction temperature not lower than the melting point, but not higher than the boiling point of the reactants is preferable.

After the coupling reaction, the reaction solution is added to and reacted with a solution in which the biological high molecular compound is dissolved to produce, for example, when the biological high molecular compound has a free amino group, an acid amide bond between the amino group and the carboxyl group in the above peptide. The reaction is carried out at a temperature usually from 0° C. to 60° C., preferably from 5° C. to 40° C., and more preferably from 22° C. to 27° C., for 5 minutes to 24 hours, preferably 1 to 16 hours, and more preferably 1 to 2 hours.

The reaction products obtained by any of the above methods are purified by dialysis, desalting column, and the like to obtain a bound substance of the peptide and biological high molecular compound (hereinafter referred to as "bound substance").

Description now follows hereinbelow about the method for preparing the antibody (monoclonal antibody) of the present invention, using the bound product thus obtained above as an antigen. For the preparation of the antibody, herein, known methods can be utilized, appropriately, which are described in for example Zoku Seikagaku Jikken Koza (Biochemical Experimental Lecture Series), and Men-eki Seikagaku Ho (Immuno-Biochemistry Research Method) (Nihon Seikagaku Gakkai hen (Japan Biochemical Association, ed.)) and the like.

As a specific immunization method, the following can be given. First, the bound substance is dissolved in a sodium phosphate buffer solution (hereinafter referred to as "PBS"). Next, the solution is mixed with a Freund's complete adjuvant, incomplete adjuvant, or an assisting agent such as alum to obtain a first antigen, with which an animal is immunized.

As the animal to be immunized, any animals commonly used in the art, for example, mammals such as a mouse, rat, rabbit, goat, and horse can be used. The method of administering the immunogen for the immunization may be subcutaneous injection, intraperitoneal injection, intravenous injection, intradermal injection, or intramuscular injection, with subcutaneous injection and intraperitoneal injection being preferable. For immunization, the immunogen is administered one time or two or more times at an appropriate interval, preferably two or more times at an interval of one to five weeks.

Finally, according to a conventional manner, an immune cell obtained from the animal immunized as above is fused with a myeloma cell to yield a hybridoma, and an antibody is isolated from the said cultured hybridoma. Then, the antibody is subjected to screening utilizing a protein or polypeptide of which the C-terminal amino acid sequence is YGLR (SEQ ID NO: 1); thus, the antibody of the invention can be obtained. In a specific example of screening methods, antibodies binding to a protein or polypeptide in which the C-terminal amino acid sequence is YGLR (SEQ ID NO: 1), are first recovered, and then an antibody which substantially does not bind to a protein or polypeptide containing the amino acid sequence YGLR (SEQ ID NO: 1) outside of the C-terminal is recovered. The protein or polypeptide in which the C-terminal amino acid sequence is YGLR (SEQ ID NO: 1), includes proteins such as human, murine or rat's OPN N-half as well as polypeptides such as YGLR (SEQ ID NO: 1) or VYGLR (SEQ ID NO: 17). The protein or polypeptide containing the amino acid sequence YGLR (SEQ ID NO: 1) outside of the C-terminal includes proteins such as human, murine or rat's OPN as well as polypeptides such as VYGL (SEQ ID NO: 18), SVVYGL (SEQ ID NO: 19), and SVVYG (SEQ ID NO: 20).

Thus resulting antibody of the invention recognizes a protein or polypeptide in which the C-terminal amino acid sequence is YGLR (SEQ ID NO: 1) but not a protein or polypeptide containing the amino acid sequence YGLR (SEQ ID NO: 1) outside of the C-terminal. Since this antibody recognizes only a protein or polypeptide in which the C-terminal amino acid sequence is YGLR (SEQ ID NO: 1), it can recognize hOPN N-half, etc. which has this amino acid sequence at the C-terminal. On the other hand, this antibody cannot recognize hOPN which has said amino acid sequence outside of the C-terminal and which is not cleaved by thrombin. The amino acid sequence YGLR (SEQ ID NO: 1) is involved in an amino acid sequence SVVYGLR (SEQ ID NO: 2) which is recognized by integrin α9 or integrin α4 such as α9□1, α4β1 or α4β7, and so the antibody of the invention can inhibit the binding of OPN N-half to integrin α9 or integrin α4. In addition, the antibody of the invention, since its recognition site is YGLR (SEQ ID NO: 1), can also recognize swine (Accession Number: P14287), monkey (Accession Number: XP_001093307), hamster (CAI65407), canine (ABA40758), murine (AAA57265, etc.), and rat's (BAA19247, etc.) OPN N-halfs which have said amino acid sequence.

The antibody of the invention, as mentioned above, can inhibit the binding of OPN N-half to integrin α9 or integrin α4. Since these integrins are involved in inflammatory response, a drug inhibiting the integrin activity is considered to have potentially an anti-inflammatory action. Thus, the antibody of the invention is effective in treatment of inflammatory diseases such as rheumatism, hepatitis, arthritis, and the like.

In this connection, the antibody of the invention, as shown in Examples below, can suppress necrosis of hepatocytes in the concanavalin A (hereinafter referred to as "ConA") induced hepatitis and increase of the ALT (alanine amino transferase) value. Thus, it is preferred to use the antibody of the invention as a therapeutic agent particularly for hepatitis.

Since integrins are considered to be involved cooperatively in the inflammation of rheumatism, the antibody of the invention which broadly blocks the binding of these integrins to OPN N-half can suppress deterioration of the state of rheumatism and other autoimmune diseases. Thus, the antibody of the present invention can be used as an active ingredient for therapeutic agents for rheumatoid arthritis, rheumatism such as juvenile articular rheumatism and chronic rheumatism, psoriasis arthritis, and psoriasis; the suppression of chronic rejections after organ transplantation; and the therapeutic treatment of autoimmune diseases such as systemic autoimmune diseases, erythematodes, uveitis, Behcet disease, multiple myositis, skein proliferative nephritis, and sarcoidosis.

The antibody of the present invention can be used to make the above therapeutic agents by further purifying the antibody, if necessary, which is subsequently formulated into dosage forms according to a general method. Examples of the dosage forms of these therapeutic agents include parenteral forms such as injections and infusions, which are preferably applied via intravenous injection and subcutaneous injection and the like. For the formulation, additionally, pharmaceutically acceptable carriers and additives may be used within a pharmaceutically acceptable range, depending on the dosage form. The amount of the antibody to be added for the formulation varies, depending on the symptomatic severity and age of a patient, the dosage form of the formulation to be used or the biding titer of the antibody or the like. For example, and amount of about 0.1 mg/kg to 100 mg/kg is satisfactorily used.

Further, the antibody of the present invention can be used in the immunological determination method by immobilizing or conjugating the antibody.

The conjugation of the present antibody is made with a general method by binding the antibody of the present invention with a labeling substance of enzymes such as horseradish peroxidase (referred to as "HRP" hereinafter), alkali phosphatase (referred to as "AP" hereinafter) and the like, fluorescent substances such as fluorescein isocyanate, and rhodamine and the like, radioactive substances such as $^{32}P$, $^{125}I$ and the like, chemiluminescent substances, and the like.

The immobilization of the present antibody is made by binding the antibody of the present invention with an appropriate carrier. The carrier used at the step for immobilized antibody includes, but not specifically limited to any carriers for routine use in immunochemical assay methods. The carrier can include, for example, polystyrene 96-well microtiter plate or microtiter plate of amino group-bound type. For further antibody immobilization, for example, a buffer containing the antibody is satisfactorily added to and incubated with the carrier.

OPN N-half can be measured precisely with the antibody of the present invention by combining an OPN N-half antibody (referred to as "OPN-1 antibody", hereinafter) which has different epitope from the present antibody which binds to OPN N-half cleaved by thorombin.

As the above-described antibody which specifically binds to OPN N-half cleaved by thrombin and has different epitope from the antibody of the present invention, polyclonal antibody or monoclonal antibody can be used that can be obtained by a general method, for example by using the all or part of the OPN N-half as an antigen.

There is no particular limitation in all or part of OPN N-half used as the above antigen; preferred is, for example, a polypeptide having the N-terminal amino acid sequence of OPN N-half, preferably a polypeptide comprising about 5 to 30 consecutive amino acids, more preferably about 10 to 20 amino acids, in the above-mentioned amino acid sequence. This polypeptide may be selected depending on the animal from which the OPN or OPN N-half to be measured is derived; for example, when the target for measurement is hOPN, hOPN-1 peptide corresponding to the 17th to 31st amino acid sequence (SEQ ID NO: 3) of hOPN is used; for murine OPN (hereinafter referred to as "mOPH"), mOPN-1 peptide corresponding to the 17th to 32nd amino acid sequence (SEQ ID NO: 4) of mOPN is used; and for rat's OPN (hereinafter referred to as "rOPN"), rOPN-1 peptide corresponding to the 17th to 33rd amino acid sequence (SEQ ID NO: 5) of rOPN is used. In this connection, the amino acid sequence of mOPN can be seen from Pubmed as Accession Number AAA57265, AAH02113, AAH57858, AAH80720, CAA36132 and NPO33289; in the invention, AAA57265 was employed. The amino acid sequence of rOPN can also be seen from Pubmed as AAH78874 and BAA19247; in the invention, BAA19247 was employed.

```
hOPN-1 peptide:
IPVKQADSGSSEEKQ         (SEQ ID NO: 6)

mOPN-1 peptide:
LPVKVTDSGSSEEKLY        (SEQ ID NO: 7)

rOPN-1 peptide:
LPVKVAEFGSSEEKAHY       (SEQ ID NO: 8)
```

In addition, when preparing the OPN-1 antibody using the above peptide, a bound substance of the peptide with a biological high molecular compound preparation of the above peptide may be used as an antigen in the same way as in the preparation of the antibody of the present invention. In this bound substance of the peptide with a biological high molecular compound, the peptide is preferably bound after attaching lysine-cysteine (KC), for example, to the amino acid at the C-terminal.

As the above OPN-1 antibody, the following antibodies commercially available from Immuno-Biological Laboratories Co., Ltd. can be used.
Anti-Mouse Osteopontin (O-17) Rabbit IgG Affinity Purify (Product number: 18621)
Anti-Human Osteopontin (O-17) Rabbit IgG Affinity Purify (Product number: 18625)
Anti-Rat Osteopontin (O-17) Rabbit IgG Affinity Purify (Product number: 18628)

OPN N-half can be precisely assayed by using the antibody of the present invention and the OPN-1 antibody. As specific assay methods, various methods currently used in common immunochemical measuring such as radioisotope immunoassay (RIA method), ELISA method (E. Engvall et al. (1980)), Methods in Enzymol., 70, 419-439, fluorescent antibody technique, plaque method, spot method, condensation method, Ouchterlony, immunochromatography, and the like ("Hybridoma method and monoclonal antibody" R&D planning Inc., pp 30-53, Mar. 5, 1982) can be used.

Although an appropriate method can be selected from these assay methods taking various factors into consideration, the ELISA method is preferable due to the high sensitivity, ease of assaying, and the like. A specific procedure of assaying OPN N-half will be described taking a sandwich method, which is one of the ELISA methods, as an example.

As a step (A), an antibody of the present invention is immobilized on a carrier. Next, as a step (B), the surface of the carrier on which the antibody is not immobilized is blocked with a substance irrelevant to OPN N-half, for example, a protein. As a step (C), test samples containing OPN N-half at different concentrations are added to produce a complex of the OPN N-half and the antibody of the present invention. Finally, as a step (E), the amount of the substance used as a label is measured to determine the OPN N-half in the sample using a previously prepared calibration curve. In this connection, the antibodies used in the step (A) and the step (D) may be reversed for measurement, though it is preferred to immobilize the antibody of the invention in view of the sensitivity of detection.

There are no specific limitations to the carrier used for immobilizing the antibody of the present invention in the step (A). Any carriers commonly used in immunochemical assay can be used. For example, a 96-well microtiter plate made of polystyrene or an amino group bound-type microtiter plate can be given. In order to immobilize the above antibody, a buffer solution containing the antibody, for example, is added to a carrier and incubated. As the buffer solution, known buffer solutions such as a 10 mM PBS can be given. Although the concentration of the antibody in the buffer solution can be selected from a wide range, usually a range from about 0.01 to 100 μg/ml, and preferably from 0.1 to 20 μg/ml is used. When a 96-well microtiter plate is used as a carrier, the volume per well is 300 μl or less, and preferably about 20 to 150 μl. There are also no specific limitations to the incubation conditions. Usually, incubation overnight at about 4° C. is appropriate.

Blocking in step (B) is to inhibit OPN N-half in a test sample from being adsorbed in the carrier, on which the antibody of the present invention has been immobilized in the step (A), irrespective of the antigen-antibody reaction. As a blocking agent, BSA, a skim milk solution, and commercially-available blocking agents such as "Block Ace" manufactured by Dainippon Pharmaceutical Co., Ltd. (code No. UK-25B) can be used, for example. Although not limited, a specific blocking method comprises, for example, adding an appropriate amount of Block Ace to a portion in which an antigen has been immobilized and incubating overnight at about 4° C., followed by washing with a buffer solution.

Further, the test sample containing OPN N-half is caused to come in contact with an immobilized antibody of the present invention and the OPN N-half is captured with the immobilized antibody of the present invention to produce a complex of the immobilized antibody and OPN N-half in the step (C). The conditions for producing the complex are not limited. The reaction is conducted at about 4 to 37° C. for about 1 hour to overnight. After the reaction, the carrier is preferably washed with a buffer solution to remove unreacted proteins and the like. As the buffer solution, a 10 mM PBS (pH containing 0.05% (v/v) Tween 20 is preferable.

Further, in step (D), a labeled OPN-1 antibody with which the labeling substances for use includes enzymes such as horse radish peroxidase (HRP), alkaline phosphatase (AP) and the like, fluorescent substances such as fluorescein isocyanate, and rhodamine and the like, radioactive substances such as $^{32}P$, $^{125}I$ and the like, chemiluminescent substances, and the like, is added to OPN N-half that is captured by the immobilized antibody of the present invention to produce a complex of the immobilized antibody of the present invention, OPN N-half, and the labeled OPN-1 antibody. After the reaction, the carrier is preferably washed with a buffer solution to remove unreacted proteins and the like. The same buffer solution as that described above is used for this reaction. The amount of the labeled OPN-1 antibody used in step (D) is about 5,000 to 10,000 times that of the immobilized antibody, preferably an amount diluted to a concentration in which the ultimate absorbance is 1.5-2.0. A buffer solution can be used for dilution and the reaction is carried out at about 4 to 37° C. for about 1 hour, for example. After the reaction, the complex substance is preferably washed with the buffer solution. The complex of the immobilized antibody of the present invention, OPN N-half, and the labeled OPN-1 antibody is formed by the above reaction.

In step (E), a coloring substrate solution reactive with the labeling substance used in the OPN-1 labeled antibody is added and absorbance is measured to calculate the amount of OPN N-half, in reference to a calibration curve.

When horseradish peroxidase, which is an enzyme, is used for labeling the antibody as a labeling substance, a coloring substrate solution containing hydrogen peroxide and 3,3',5, 5'-tetramethylbenzine (hereinafter referred to as "TMB") can be used, for example. Although not limited, the coloring reaction is carried out by adding the coloring substrate solution, reacting at about 25° C. for about 30 minutes, and adding a 1-2 N sulfuric acid aqueous solution to terminate the enzyme reaction. When TMB is used, the coloration is determined by measuring absorbance at 450 nm. When alkaline phosphatase enzyme is used as a labeling substance, on the other hand, p-nitrophenylphosphoric acid is used as a coloring substrate, a 2N NaOH solution is added to terminate the enzyme reaction, and the absorbance at 415 nm is measured. The concentration of OPN N-half in a sample can be calculated by using a calibration curve previously prepared using the absorbance of a reaction solution to which OPN N-half with a known concentration is added.

In order to assay OPN N-half according to the method described above, a kit for assaying OPN N-half comprising a first reagent containing the antibody of the present invention and a second reagent containing the OPN-1 antibody is preferably used. Such a kit is hereinafter referred to as "kit of the present invention".

The kit of the present invention can be prepared according to a conventional method. Specifically, the antibody of the present invention or the OPN-1 antibody as a labeled antibody, and a buffer solution for dilution, a standard substance, a buffer solution for a substrate, a termination solution, washing fluid, and the like are combined.

The OPN N-half in samples such as plasma, serum, urine, synovial fluid, etc can be precisely assayed using the assay kit obtained in this manner and the above measuring method.

Utilizing the above-mentioned method and kit for measurement, OPN N-half in the above sample, in particular, urine sample, can be measured, and the amount measured can be used as an index for diagnosis of rheumatoid arthritis. Specifically, first, urine is collected from a number of healthy subjects or patients of rheumatoid arthritis, and the concentration of urinary OPN N-half is measured using the above method or kit for measurement to calculate the mean value. Subsequently, the concentration of urinary OPN N-half of a subject is measured; when the value is significantly higher than the mean value of healthy persons (for example, 1500 pM or higher) or significantly not lower than the mean value of the patients of rheumatoid arthritis (for example, lower than 1500 pM), the subject can be diagnosed to be suffering from rheumatoid arthritis.

Further, utilizing the above-mentioned method and kit for measurement, OPN N-half in the above sample, in particular, synovial fluid, can be measured, and the amount measured can be used as an index for distinguishing rheumatoid arthritis from osteoarthritis. Specifically, first, synovial fluid is collected from a number of patients suffering from osteoarthritis or rheumatoid arthritis, and the OPN N-half concentration is measured using the above method or kit for measurement to calculate the mean value. Subsequently, the OPN N-half concentration of a subject is measured; when the value is significantly higher than the mean value of the osteoarthritis patients (for example, 200 pM or higher) or significantly not lower than the mean value of the patients of rheumatoid arthritis (for example, lower than 200 pM), the subject can be diagnosed to be suffering from rheumatoid arthritis. In this differentiation, the OPN concentration in synovial fluid is measured, from which the ratio of OPN N-half to the total OPN(OPN plus OPN N-half) is calculated; the result may be used in distinguishing together with the data. Specifically, in this example, when the ratio of OPN N-half to the total OPN in the synovial fluid is 8.52% or higher, the subject may be diagnosed to be suffering from rheumatoid arthritis. The OPN concentration in the synovial fluid can be measured with a commercially available kit for OPN measurement (e.g., Human Osteopontin Assay Kit (L)-IBL (made by Immuno-Biological Laboratories Co., Ltd. (Product no. 27158))).

Further, since the amount of OPN N-half is considered to correlate with the grade of osteoarthritis, this can be used as an index to judge the severity of osteoarthritis in addition to the above distinguishing method. Specifically, the OPN N-half concentration in the synovial fluid is higher in the medium or high severity than in a milder case (55.0 pM of the mean value for a milder case versus 163.9 pM in the medium severity and 142.2 pM in the high severity). In addition, since the ratio of OPN N-half to the total OPN(OPN plus OPN N-half) in the synovial fluid is also considered to correlate with the grade of osteoarthritis, the result may be used in judgment of the severity of osteoarthritis in combination with the above data. Specifically, in this example, when the ratio of OPN N-half to the total OPN in the synovial fluid is 0.93% or lower, the subject is judged to be suffering from milder osteoarthritis, and when it is 1.81% or higher, the subject is judged to be suffering from middle or highly severe osteoarthritis.

Since the antibody of the invention specifically recognizes a protein or polypeptide in which the C-terminal amino acid sequence is YGLR (SEQ ID NO: 1), the protein or polypeptide recognized by the above antibody can be used as a tag in detection or purification of desired proteins in the same way as in the well-known tag such as His tag or Flag tag.

Specifically, in detection of the desired protein, first, a polynucleotide coding for a peptide or polypeptide in which the C-terminal amino acid sequence is YGLR (SEQ ID NO: 1) and a polynucleotide coding for the target protein to be detected are prepared in a conventional manner, and these polynucleotides respectively are integrated into a vector to yield a recombinant vector. Subsequently, the resulting vector is expressed in a well-known protein expression system to yield a recombinant protein containing the target protein and the protein or polypeptide in which the C-terminal amino acid sequence is YGLR (SEQ ID NO: 1). Finally, this recombinant protein is detected by the labeled antibody of the invention in a conventional manner.

The vector used in detection of the above target protein includes pEU vector when the expression system for protein is a cell-free synthetic system using a wheat germ extract solution. In this case, it is preferable to insert a polynucleotide into the vector, said polynucleotide coding for a protein or polypeptide in which the C-terminal amino acid sequence is YGLR (SEQ ID NO: 1) and linking to the 3'-terminal of a polynucleotide coding for the target protein. It is also preferable to use a polynucleotide into which a promoter such as SP6 is introduced at the 5'-terminal.

As for the vector used in detection of the above target protein, pGEX vector, pQE vector, and the like are included when the expression system for the protein is a cell synthetic system using *Escherichia coli*.

On the other hand, in purification of the target protein, in the same manner as mentioned above, the recombinant protein containing the target protein and the protein or polypeptide in which the C-terminal amino acid sequence is YGLR (SEQ ID NO: 1) is expressed in a well-known expression system for protein, and bound to the antibody of the invention immobilized on a carrier. Then, the binding is dissociated with 0.1M glycine-HCl buffer (pH 2.5) to give a pure recombinant protein.

In purification of the above target protein, as a carrier used in immobilization of the antibody of the invention, Formyl-cellulofine (made by Seikagaku Corp.) may be used; immobilization is achieved by means of utilizing an amino group.

EXAMPLES

The present invention will be described in more detail by examples, which should not be construed as limiting the present invention. Any person having an ordinary skill in the art can easily modify or alter the inventions based on the description in this specification. Such modifications and alterations are included in the technological scope of the present invention.

Reference Example 1

Preparation of Polypeptide for Antigen

Polypeptides for antigen were purchased from Synpep Corporation and TANA Laboratories, USA. The amino acid sequences of these polypeptides are shown in (a), (b), and (c) below. The polypeptide (a) has cysteine (C) attached to amino acid sequence consists of continuous amino acid sequence from C-terminal to N-terminal of the OPN N-half (amino acid sequence corresponding to 162-168 of the amino acid sequence of hOPN N-half (hereinafter referred to as "hOPN-7 peptide")). The polypeptide (b) has cysteine (C) attached to amino acid sequence corresponding to 17-31 of the amino acid sequence of hOPN N-half. The polypeptide (c) has cysteine (C) attached to amino acid sequence corresponding to 153-169 of the amino acid sequence of full length hOPN.

```
Polypeptide (a):
CSVVYGLR              (Sequence ID No. 9)

Polypeptide (b):
IPVKQADSGSSEEKQC      (Sequence ID No. 10)

Polypeptide (c):
CVDTYDGRGDSVVYGLRS    (Sequence ID No. 11)
```

Reference Example 2

Preparation of Antigen for Immunization

Bound substances of each of the above polypeptide and thyroglobulin were prepared by the EMCS (N-(6-Maleimidocaproyloxy)-succinimide) method as follows. The molar ratio of the thyroglobulin, polypeptide, and EMCS used for preparing the bound substances was 1:300:400 respectively.

First, 4 mg of each peptide of Example 1 was dissolved in about 1 ml of distilled water. A solution of 5 mg of thyroglobulin in 1 ml of a 0.01 M phosphoric acid buffer (pH 7.0) and a solution of 80 mg/ml EMCS dissolved in dimethylformamide were mixed in an amount to obtain a thyroglobulin-_EMCS complex solution containing the thyroglobulin and EMCS at the above molar ratio. This complex solution was divided into three portions, to each of which was added each polypeptide solution in an amount to make the above molar ratio, thereby obtaining a solution of a bound substance of the polypeptide crosslinked by EMCS and the thyroglobulin.

This bound substance solution was dialyzed using PBS to obtain a solution with a bound substance concentration of 10 mg/ml. The bound substances of each peptide and thyroglobulin obtained in this manner were used as antigens for immunization in the following examples.

Example 1

Production of Monoclonal Antibody:

The bound substance of the polypeptide (a) and thyroglobulin obtained in Reference Example 2, was then used for murine immunization to the BALB/c mouse as an immunoantigen according to a general method. The bound substance was immunized by administering 4 times to the mouse. Spleen monocyte cells of the immunized mouse and a fusion partner, X63-Ag8-653, were subjected to polyethylene glycol-mediated cell fusion and hybridomas were selected using the method described in J. Immunol. 146: 3721-3728. In selecting the hybridomas, cells that react with immobilized peptide (a) were selected, and as a result, hybridoma called 39E1 and 34E3 were obtained.

The hybridomas selected in this manner were cultured in a serum-free GIT culture medium (manufactured by Wako Pure Chemical Industries, Ltd.) to produce antibodies until 80% of the cells were extinct. Next, after removing the cells from the culture medium by centrifugation (1,000 rpm, 15 min), the resultant fluid was brought to a 50% saturated state with ammonium sulfate, allowed to standstill at 4° C. overnight, and the resultant precipitate was collected by centrifugation (1,000 rpm, 30 min). After dissolving the precipitate in a two-fold diluted binding buffer (manufactured by Protein AMAPS IIkit), IgG was adsorbed in Protein A column (manufactured by Pharmacia Amersham). The products were purified by PBS dialysis overnight to obtain antibodies recognizing the polypeptides including the C terminal of human OPN N-half from each hybridoma. These antibodies were named 39E1 antibody and 34E3 antibody respectively. The hybridoma generating the monoclonal antibody 34E3 was deposited as FERM BP-10897 as international deposit at the Patent Organism Depository Center, the National Institute of Advanced Industrial Science and Technology (AIST Tsukuba Central 6, 1-1-1, Higashi Tsukuba-shi, Ibaraki 305-8566, Japan) on the date of Jul. 11, 2006 (This deposition was originally deposited as FERM P-20957 and transferred to international deposit on the date of Jul. 11, 2006).

Reference Example 3

Preparation of Polyclonal Antibody (1)

A conjugate of the polypeptide (b) obtained in Reference Example 2 with thyroglobulin was used as an immunogen; this was administered as a solution (100 mg,/ml) at a dose of 50 μl to a rabbit for immunization at an interval of 1 week or 2 weeks. The antigen was mixed with a Freund's complete adjuvant only in the first immunization, and from the second immunization a Freund's incomplete adjuvant was mixed. Thereafter, the whole blood was collected and centrifuged at 1,500 rpm for 15 minutes to yield an antiserum as rabbit's polyclonal antibody (hereinafter referred to as "hOPN-1 antibody").

Reference Example 4

Preparation of Polyclonal Antibody (2)

A conjugate of the polypeptide (c) obtained in Reference Example 2 with thyroglobulin was used as an immunogen with mice as animal to be immunized; otherwise, the same procedure as in Reference Example 3 was performed to yield a murine polyclonal antibody (hereinafter referred to as "hOPN-5 antibody").

Reference Example 5

Preparation of OPN

In preparing hOPN, a gene of hOPN (Accession Number: J04765) was integrated into a vector pcDNA3.1 in a conventional manner (e.g., "Bunshi Seibutugaku Kisojikken Hou (Basic Experiment in Molecular Biology), Nankodo Co., Ltd."), and the resulting vector was transfected into a Chinese hamster ovary (CHO) cell. Then, the cell was incubated, and the incubated supernatant was purified on a column of anti-OPN-1 antibody (made by Immuno-Biological Laboratories Co., Ltd.) to yield hOPN. This hOPN was treated with thrombin at 37° C. for 90 minutes to yield OPN N-half. Further, mOPN and rOPN were respectively treated with thrombin in the same manner as above to yield N-halfs of mOPN and rOPN, respectively.

Example 2

Confirmation of Antibody Specificity by Western Blotting:

In order to confirm the specificity of the 39E1 antibody and the 34E3 antibody obtained in Example 1, Western blotting was performed in a conventional manner (e.g., "Bunshi Seibutugaku Kisojikken Hou (Basic Experiment in Molecular Biology), Nankodo Co., Ltd."). In performing the western blotting, hOPN or hOPN N-half prepared in Reference Example 5, hOPN or hOPN N-half treated with addition of thrombin at 37° C. for 90 minutes (Thrombin (+)), and hOPN or hOPN N-half treated with addition of no thrombin (Thrombin (−)) were used. As a control, the western blotting was performed in the same manner using the hOPN-1 antibody prepared in Reference Example 3 and the hOPN-5 antibody prepared in Reference Example 4, in which the polypeptides used in immunization were different. FIG. 1 shows the results.

FIG. 1 shows the results that the 39E1 antibody and 34E3 antibody do not react with hOPN but only with hOPN N-half. On the other hand, the hOPN-1 antibody and hOPN-5 antibody reacted with both of hOPN and hOPN N-half. These results indicate that the 39E1 antibody and 34E3 antibody are specific antibodies which specifically react only with OPN N-half.

Example 3

Confirmation of Cross-Reactivity of Antibodies by Western Blotting:

FIG. 2 shows the results of the western blotting conducted on mOPN and rOPN using the above 39E1 antibody and 34E3 antibody. As a control, the western blotting was performed in the same manner as above using an antibody (hereinafter referred to as "mOPN-5 antibody") prepared from the following polypeptide (d) as antigen (138th to 153rd amino acid sequence of mOPN, attached with cysteine (C)) as described in the International Patent Application filed by the applicant of the present invention (WO 02/081522 pamphlet). The results are also shown in FIG. 2.

Polypeptide (d): CVDVPNGRGDSLAYGLR (SEQ ID NO: 12)

FIG. 2 shows that the 39E1 antibody and 34E3 antibody react not only with hOPN N-half but also with mOPN N-half and rOPN N-half. This indicates that the 39E1 antibody and 34E3 antibody have a cross-reactivity to hOPN N-half, mOPN N-half and rOPN N-half and that the recognition site of these antibodies is in the common amino acid sequences of the C-terminals in hOPN N-half, mOPN N-half and rOPN N-half.

Example 4

Development of Sandwich ELISA:
(1) Preparation of a Conjugate of hOPN-1 Antibody and HRP A conjugate of hOPN-1 antibody prepared in Reference Example 3 and horse radish peroxidase (HRP) was prepared as follows. A necessary amount of HRP was dissolved in distilled water and oxidized with NaIO$_4$, followed by dialysis in 1 mM acetate buffer (pH 4.4) overnight. On the other hand, 2 mg of hOPN-1 antibody was dialyzed in 0.1M carbonate buffer (pH 9.5) overnight. The dialyzed hOPN-1 antibody and HRP were mixed at the ratio of 0.4 mg of HRP to 1 mg of antibody and allowed to react at room temperature for 2 hours. Then, NaBH$_4$ was added, and the mixture allowed to react in ice for 2 hours and then dialyzed in PBS overnight. The reaction mixture was then subjected to gel-filtration to yield a conjugate of hOPN-1 antibody and HRP (hereinafter referred to as "hOPN-1 labeled antibody").

(2) Preparation of a Sandwich ELISA Plate

Into a 96-well ELISA plate was added 100 μl each of 10 μg/ml 39E1 antibody or 34E3 antibody; in the same manner, hOPN-5 antibody was added for comparison. This was then allowed to react at 4° C. overnight, and then blocked with 1% BSA/PBS/NaN$_3$ solution to yield a sandwich ELISA plate on which 39E1 antibody or 34E3 antibody was immobilized. In this connection, the conjugate of hOPN-1 antibody and HRP was used as a labeled antibody.

(3) Preparation of a Standard Curve

Using the 96-well ELISA plate prepared in the above process (2) and the hOPN-1 labeled antibody prepared in the above process (1), hOPN (Thrombin (−)) and hOPN N-half (Thrombin (+)) were measured. As a control, hOPN was measured. These results are shown in FIG. 3. When hOPN N-half was measured using the 39E1 antibody or 34E3 antibody and the hOPN-1 labeled antibody, a good linearity was respectively obtained depending on the concentration. The cross reactivity with hOPN was about 0.39%, respectively. On the other hand, when hOPN N-half was measured using the hOPN-5 antibody and the hOPN-1 labeled antibody, a good linearity was also obtained depending on the concentration, but the cross reactivity with hOPN reached as large as about 25%.

Example 5

Test of the Inhibitory Activity for Cell Adhesion:
(1) Adhesion Test for Murine Melanoma Cells Using a murine melanoma cell strain B16-F10 (donated by Hokkaido University) containing integrin α9 and α4, a polypeptide having a cell adhesive property was assayed according to the following method from the following polypeptides. Among the polypeptides, in the amino acid sequence (SEQ ID NO: 4) of mOPN, polypeptide corresponding to the 17th to 32nd amino acid sequence (mOPN-1 peptide), polypeptide corresponding to the 155th to 172nd amino acid sequence (mOPN-3 peptide), polypeptide corresponding to the 147th to 153rd amino acid sequence (mOPN-7 peptide), polypeptide corresponding to the 138th to 153rd amino acid sequence (mOPN-5 peptide), and polypeptide corresponding to the 143rd to 147th amino acid sequence (GRGDS (SEQ ID NO: 16) peptide), were purchased from Synpep Corporation, TANA laboratories, USA, and Auspep. The full length OPN (Full mOPN) and murine OPN N-half (mOPN-N) were respectively prepared in the same manner as mentioned in Reference Example 5.

mOPN-1 peptide: LPVKVTDSGSSEEKLY (SEQ ID NO: 7)
mOPN-3 peptide: KSRSFQVSDEQYPDATDE (SEQ ID NO: 13)
mOPN-5 peptide: VDVPNGRGDSLAYGLR (SEQ ID NO: 14)
mOPN-7 peptide: SLAYGLR (SEQ ID NO: 15)
GRGDS (SEQ ID NO: 16) peptide; GRGDS (SEQ ID NO: 16)

The above polypeptides or proteins were respectively adjusted with 0.1M carbonate buffer (pH 9.5) so as to be the concentration of 20 μg/ml, and 50 μl/well each was placed in a 96-well ELISA plate. Then, the plate was allowed to react at 4° C. overnight, then blocked with 0.5% BSA/PBS/NaN$_3$ solution, and washed with PBS to yield an ELISA plate on which the above polypeptides or proteins were immobilized. Next, the B16-F10 cells were adjusted at 1×10$^5$ cells/ml with 0.25% BSA/D-MEM, and 200 μl each was placed on the above ELISA plate, then incubated at 37° C. for 1 hour, and washed with 0.25% BSA/D-MEM to remove the unbound cells from the plate. Then, 20% methanol solution containing 0.5% crystal violet was added to each well to dye for 30 minutes. All of the wells were rinsed 3 times with water and the adhered cells were dissolved and transferred with 20% acetic acid. The absorbance of the supernatant in each well was measured at 590 nm to count the relative number of the cells which adhered to the well and analyzed by an immunoreader. The results are shown in FIG. 4.

FIG. 4 indicates that the murine melanoma cell strain containing integrins □9 and □4 hardly adheres to polypeptides containing no GRGDS (SEQ ID NO: 16) amino acid sequence, i.e., mOPN-1 peptide and mOPN-3 peptide.

It was examined according to the following method whether or not the 39E1 antibody, 34E3 antibody or mOPN-5 antibody inhibits adhesion of the cells to the polypeptides contained in mOPN (mOPN-5 peptide, mOPN-7 peptide and GRGDS (SEQ ID NO: 16) peptide). First, a 96-well plate was pre-coated with mOPN-5, mOPN-7 and GRGDS (SEQ ID NO: 16) peptides, respectively, in a variety of concentrations at 4° C. overnight, and then treated with 0.5% BSA/PBS at 37° C. for 10 minutes to block non-specific adhesion. Next, the murine melanoma cell B16-F10 was suspended in D-MEM containing 0.25% BSA, and the resulting cell suspension (cell concentration 5×10$^4$ cells/well) 200 μl was poured in a 96-well plate in the presence or absence of a variety of concentrations of the above antibody, and incubated at 37° C. for 1 hour. After incubation, the culture medium was removed from the plate, and all of the wells were washed twice with D-MEM containing 0.25% BSA. The adhered cells were fixed and dyed with 0.5% crystal violet in 20% methanol for 30 minutes. All of the wells were rinsed 3 times with water, and the adhered cells were dissolved and transferred with 20% acetic acid. The absorbance of the supernatant in each well was measured at 590 nm to count the relative number of the cells which adhered to the well and analyzed by an immunoreader. The results are shown in FIG. 5.

FIG. 5 shows that the 39E1 antibody and 34E3 antibody inhibit adhesion of a murine melanoma cell strain to mOPN-5 and mOPN-7. On the other hand, since the 39E1 antibody and 34E3 antibody had no influence on adhesion of a murine melanoma cell strain to the GRGDS (SEQ ID NO: 16) peptide, it was confirmed that the 39E1 antibody and 34E3 antibody inhibited adhesion of mOPN and integrins α4 and α9. In FIG. 5, however, the mOPN-5 antibody which was obtained by using as antigen the polypeptide (d) containing the GRGDS (SEQ ID NO: 16) peptide did not inhibit adhesion of the GRGDS (SEQ ID NO: 16) peptide to a murine melanoma cell strain; the reason is that the mOPN antibody cannot recognize a short-length GRGDS (SEQ ID NO: 16) peptide.

Example 6

Development of a Purification System Using 39E1 Antibody and 34E3 Antibody:

The following experiment was performed to show that the recognition sites of the 39E1 antibody and 34E3 antibody are in the amino acid sequence consecutive from the C-terminal amino acid to the N-terminal side of OPN N-half. First, 5 patterns of primers (anti-sense primers) were prepared, which were respectively designed to have polynucleotides coding for the following polypeptides (I)-(V) containing 5 different parts in the hOPN-7 peptide used in preparation of the 39E1 antibody and 34E3 antibody at the 3' end, and further polynucleotides coding for the C-terminal portions having optional polypeptide sequences to which the polypeptides (I)-(V) are expected to bind at the 5' end. As the sense primers, primers for SP6 promoter were prepared. In the PCR method using these anti-sense primers and sense primers, the sequences from the promoter to the 3' end necessary for synthesis of mRNAs were synthesized. Further, mRNAs were synthesized using the PCR product as template, and proteins corresponding to the respective base sequences were synthesized in a cell-free synthetic system using a wheat germ extract solution (made by Cell Free Science). Using the 39E1 antibody and 34E3 antibody together with the synthesized respective proteins and hOPN N-half as control, the western blotting was conducted. As a control, the western blotting was conducted in the same manner using a monoclonal antibody 2K1 prepared with the above polypeptide (c) as antigen as described in WO02/081522 pamphlet reported by the applicant of the present invention. The results are shown in FIG. 6.

```
Polypeptide (I):      YGLR      (SEQ ID NO: 1)
Polypeptide (II):     VYGLR     (SEQ ID NO: 17)
Polypeptide (III):    VYGL      (SEQ ID NO: 18)
Polypeptide (IV):     SVVYGL    (SEQ ID NO: 19)
Polypeptide (V):      SVVYG     (SEQ ID NO: 20)
```

FIG. 6 shows the results that the 39E1 antibody and 34E3 antibody recognize the polypeptides (I), (II) and hOPN N-half which contain the C-terminal amino acid R of hOPN N-half and a consecutive amino acid sequence from R toward the N-terminal, but they do not recognize the polypeptides (III)-(V) which contain no amino acid R at the C-terminal of hOPN N-half. On the other hand, the 2K1 antibody as a result could not recognize any of the polypeptides (I)-(V) and hardly recognized hOPN N-half. From these results, it was found that the 39E1 antibody and 34E3 antibody recognize the C-terminal amino acid R of hOPN N-half cleaved by thrombin and are useful in detection of or as purification tags of polypeptides or proteins.

Example 7

Measurement of the Amount of Urinary OPN N-Half in Patients Of Chronic Rheumatoid Arthritis (RA) by ELISA:

Urine was collected from 23 healthy subjects and 25 RA patients from whom informed consent had been obtained, and the concentrations of the full-length OPN and of OPN N-half were measured using a Human Osteopontin Assay Kit (L)-IBL (made by Immuno-Biological Laboratories Co., Ltd. (Product no. 27158))) and the ELISA system prepared in Example 4. The concentrations of the full-length OPN and the OPN N-half in the urine samples are indicated by pM, and the value was presented by mean±standard error. Table 1 shows the results of measured concentrations.

TABLE 1

|  | Full length OPN conc. in Urine (µM) | OPN N-half conc. in Urine (pM) | Significant difference* (p Value) |
|---|---|---|---|
| Healthy Subj. | 381.4 ± 59.3 | 801.5 ± 178.4 | — |
| RA Patient | 288.1 ± 48.8 | 2128.4 ± 429.4 | p < 0.01 |

*Significant difference of OPN N-half concentration to healthy subjects; student's t-test The results of measurement indicate that there is no statistically significant difference between the healthy subjects and the RA patients for the full-length OPN concentration in urine, and the OPN N-half concentration in urine was 801.5±178.4 pM for the healthy subjects and 2128.4±429.4 pM for the RA patients, indicating that the latter value was significantly higher than the urinary concentration in the healthy subjects.

From these results, it became clear that the urinary OPN N-half can be measured as a new marker of chronic rheumatoid arthritis by means of the said kit; thus, the kit of the invention allows a non-invasive examination utilizing a urine sample.

Example 8

Measurement of OPN N-Half in the Knee Synovial Fluid by ELISA in the Patients Suffering from Osteoarthritis (OA) and Chronic Rheumatoid Arthritis (RA):

The synovial fluid of 107 knees of osteoarthritis (OA) and that of 18 knees of rheumatoid arthritis (RA) were recovered and respectively preserved under freezing at −80° C. OA included 45 joints of mild cases corresponding to the grades 1 and 2 of Kellgren & Lawrence, 33 joints of medium cases corresponding to the grade 3, and 29 joints of severe cases corresponding to the grade 4. RA includes the severe cases of the grades III, IV and V of the Larsen classification. The synovial fluid was diluted 10-fold, in which the OPN N-half concentration was determined by the ELISA kit prepared in Example 4. For comparison, the concentration of the full-length OPN was determined by means of the Human Osteopontin Assay Kit (L)-IBL (made by Immuno-Biological Laboratories Co., Ltd. (Product no. 27158))). Further, the values of OPN N-half/OPN N-half+the full-length OPN (amount of OPN N-half/total amount of OPN) were calculated. Table 2 shows the results.

TABLE 2

|  |  | n | Full-length OPN (nM) | OPN-N half (pM) | OPN N half + OPN full (nM) | OPN N-half/ OPN N-half + OPN Full (%) |
|---|---|---|---|---|---|---|
| OA | All | 107 | 7.16 | 112.2 | 7.28 | 1.54% |
|  | Mild | 45 | 5.86 | 55.0 | 5.92 | 0.93% |
|  | Medium | 33 | 8.89 | 163.9 | 9.05 | 1.81% |
|  | Severe | 29 | 7.22 | 142.2 | 7.36 | 1.93% |
| RA |  | 18 | 13.23 | 1231.9 | 14.46 | 8.52% |

Comparison of OA with RA:
    Full-length OPN, no significant difference
    OPN N-half, high value in RA (p=0.0001)
    OPN N-half+Full-length OPN, no significant difference
    OPN N-half/OPN N-half+Full-length OPN, high value in RA (p<0.0001)
Comparison Between the Grades of OA:
    Full-length OPN, no significant difference
    OPN N-half, positive correlation with the grades (p=0.0037; r=0.282); higher values in medium and severe grades than in mild grade (p=0.0363)
    OPN N-half/OPN N-half+Full-length OPN, positive correlation with the grades (p=0.0048; r=0.274); higher values in medium and severe grades than in mild grade (p=0.0189)
    From these results, measurement of the OPN N-half concentration in the synovial fluid or calculation of the ratio of the amount of OPN N-half to the total amount of OPN allow the distinguishment of OA from RA and the judgment of severity of OA.

Example 9

Detection of the Amount of OPN N-Half in the Knee Synovial Fluid in the Patients by the Western Blotting:

Among the synovial fluids collected from the knees of patients in Example 8, OPN N-half was detected by means of the western blotting method using the OPN N-half antibody of the present application on the fluids in which the OPN N-half value was higher and on the fluids in which nearly no OPN N-half was detected in detection by ELISA in Example 8. More specifically, 0.15 ml of the knee synovial fluid was diluted 2-fold with D-PBS, to which was added 20 μl DEAE Sepharose Fast Flow (made by Amersham Pharmacia Biotech), and the mixture was agitated at room temperature for 30 minutes. This was then washed 5 times with 1.0 ml of PBS, and eluted with 0.1 ml of 0.7M sodium chloride/PBS solution. Further, this was mixed with 2 equivalents of sodium dodecylsulfate (SDS) buffer, subjected to boiling treatment, and used as a sample for western blotting. This sample was subjected to western blotting in a conventional manner (e.g., "Bunshi Seibutugaku Kisojikken Hou (Basic Experiment in Molecular Biology), Nankodo Co., Ltd.") using the 34E3 antibody obtained by Example 1.

In the knee synovial fluids of the patients in whom the amount of OPN N-half showed high values in ELISA in Example 8, the band of OPN N-half was also observed in the western blotting method depending on the concentration. On the other hand, in the knee synovial fluid in which nearly no value was recognized in ELISA, no band of OPN N-half was also observed in the western blotting method.

Example 10

Administration of 34E3 Antibody to Hepatitis Model Mice:

To C57BL/6 mice was administered intravenously 200 μg/mouse of Con A to develop hepatitis. Three hours before administration of Con A, 400 μg/mouse of 34E3 antibody or a control antibody was administered intravenously. After a lapse of 24 hours from administration of Con A, sera were collected, and the ALT value was determined.

In a group to which 34E3 antibody was administered, significant decrease of the ATL level was observed in comparison with the group to which a control antibody was administered. From this result, it was found that the 34E3 antibody could suppress necrosis of the hepatocytes induced by administration of Con A.

Industrial Applicability

The antibody of the invention which recognizes the C-truncated peptide of OPN(OPN N-half) cleaved by thrombin recognizes OPN cleaved by thrombin but not the full-length OPN. And the kit for measurement of OPN N-half utilizing it allows precise determination of OPN N-half, different from so far commercialized kits for measurement of OPN.

Thus, the kit of the invention for measurement can be utilized in diagnosis of inflammatory diseases in which OPN is involved, or in investigation of the mechanism of occurrence of these diseases. In addition, the antibody per se can be used as a therapeutic agent for inflammatory diseases as an antibody medicament. Further, the antibody can be utilized as a tag for purification of OPN N-half and other C-truncated peptides of thrombin-cleaved OPN.

BRIEF DESCRIPTION OF DRAWINGS

FIG. 1 shows the results of the western blotting for 34E3 antibody, 39E1 antibody, hOPN-1 antibody and hOPN-5 antibody (wherein the lane 1 shows hOPN; lane 2 hOPN Thrombin (−); lane 3 hOPN Thrombin (+); lane 4 hOPN N-half; lane 5 hOPN N-half Thrombin (−); lane 6 hOPN N-half Thrombin (+)).

FIG. 2 shows the western blotting using the 34E3 antibody, 39E1 antibody and mOPN-5 antibody.

FIG. 3 shows the results of measurement of hOPN N-half (Thrombin (+)), hOPN (Thrombin (−)) and control (hOPN) using the ELISA plate prepared in Example 4 (wherein A indicates the results of measurement with the hOPN-5 antibody and hOPN-1 labeled antibody; B indicates the results of measurement with the 34E3 antibody and hOPN-1 labeled antibody; and C indicates the results of measurement with the 39E1 antibody and hOPN-1 labeled antibody).

FIG. 4 shows the results of a test on adhesion of a variety of polypeptides derived from murine OPN to the murine melanoma cell strain B16-F10.

FIG. 5 shows the results of measurement of the adhesion inhibitory activity of the 34E3 antibody (34E3), 39E1 antibody (39E1) and mOPN-5 antibody (M-5) to a variety of polypeptides derived from murine OPN (wherein A indicates the result of adhesion inhibitory test using the mOPN-5 peptide; B indicates the result of adhesion inhibitory test using the mOPN-7 peptide; and C indicates the result of adhesion inhibitory test using the GRGDS (SEQ ID NO: 16) peptide).

FIG. 6 shows the western blotting using the 34E3 antibody, 39E1 antibody and hOPN-5 antibody together with a variety of polypeptides or proteins (wherein lane 1 indicates -mRNA; 2 cDNA; 3 cDNA-YGLR (SEQ ID NO: 1); 4 cDNA-VYGLR (SEQ ID NO: 17); 5 cDNA-VYGL (SEQ ID NO: 18); 6 cDNA-SVVYGL (SEQ ID NO: 19); 7 cDNA-SVVYG (SEQ ID NO: 20); and 8 purified hOPN N-half).

The invention claimed is:

1. An isolated or purified monoclonal antibody 34E3 which is produced by a hybridoma deposited as FERM BP-10897, wherein the isolated or purified monoclonal antibody 34E3 recognizes a protein or a polypeptide in which the C-terminal amino acid sequence is YGLR (SEQ ID NO: 1) but substantially does not recognize a protein or a polypeptide which has the amino acid sequence YGLR outside of the C-terminal.

2. The isolated or purified monoclonal antibody 34E3 according to claim 1, wherein the protein or the polypeptide in which the C-terminal amino acid sequence is YGLR (SEQ ID NO: 1) is the N-terminal fragment of osteopontin cleaved by thrombin, and the protein or the polypeptide which has the amino acid sequence YGLR outside of the C-terminal is osteopontin.

3. The isolated or purified monoclonal antibody 34E3 according to claim 1, which inhibits the binding of the N-terminal fragment of osteopontin cleaved by thrombin with integrin α9 or integrin α4.

4. The isolated or purified monoclonal antibody 34E3 according to claim 1, which recognizes the N-terminal fragment of osteopontin cleaved by human, swine, monkey, hamster, canine, murine or rat thrombin.

5. A kit for measuring the N-terminal fragment of osteopontin cleaved by thrombin, wherein the kit comprises:

a first reagent comprising the isolated or purified monoclonal antibody 34E3 according to claim 1; and a second reagent comprising an antibody of which the recognition site is different from that of the isolated or purified monoclonal antibody 34E3 contained in the first reagent and which recognizes the N-terminal fragment of osteopontin cleaved by thrombin.

6. The kit according to claim 5, which is for distinguishing rheumatoid arthritis from osteoarthritis.

7. The kit according to claim 5, which is for determining the severity of osteoarthritis.

8. A method for measuring the N-terminal fragment of osteopontin cleaved by thrombin, which comprises measuring the N-terminal fragment of osteopontin cleaved by thrombin in a sample with the isolated or purified monoclonal antibody 34E3 according to claim 1.

9. A composition comprising:
the isolated or purified monoclonal antibody 34E3 according to claim 1; and
a pharmaceutically acceptable excipient.

10. A method for treating hepatitis, wherein the method comprises administering to a subject in need thereof a therapeutically effective amount of the composition according to claim 9.

11. A method for suppressing necrosis of hepatocytes, wherein the method comprises administering to a subject in need thereof a therapeutically effective amount of the composition according to claim 9.

12. A method for treating rheumatoid arthritis, wherein the method comprises administering to a subject in need thereof a therapeutically effective amount of the composition according to claim 9.

13. A hybridoma deposited as FERM BP-10897, which produces the isolated or purified monoclonal antibody 34E3 according to claim 1.

* * * * *

UNITED STATES PATENT AND TRADEMARK OFFICE
CERTIFICATE OF CORRECTION

PATENT NO. : 7,981,672 B2
APPLICATION NO. : 12/440645
DATED : July 19, 2011
INVENTOR(S) : Hiroko Kobayashi et al.

It is certified that error appears in the above-identified patent and that said Letters Patent is hereby corrected as shown below:

Column 6, line 36, "α9□1" should read -- $\alpha 9\beta 1$ --

Column 16, line 30, "□9 and □4" should read -- $\alpha 9$ and $\alpha 4$ --

Signed and Sealed this
Tenth Day of January, 2012

David J. Kappos
*Director of the United States Patent and Trademark Office*